United States Patent
Asai

(10) Patent No.: US 7,795,546 B2
(45) Date of Patent: Sep. 14, 2010

(54) THERMOSTATIC APPARATUS AND COVER

(75) Inventor: Yasuhiro Asai, Suita (JP)

(73) Assignee: Sanyo Electric Co., Ltd., Moriguchi-shi (JP)

( * ) Notice: Subject to any disclaimer, the term of this patent is extended or adjusted under 35 U.S.C. 154(b) by 51 days.

(21) Appl. No.: 12/360,146

(22) Filed: Jan. 27, 2009

(65) Prior Publication Data

US 2009/0188714 A1 Jul. 30, 2009

(30) Foreign Application Priority Data

Jan. 30, 2008 (JP) ............................. 2008-018622

(51) Int. Cl.
*H01L 23/02* (2006.01)
(52) U.S. Cl. ........................... 174/539; 174/50; 174/650
(58) Field of Classification Search .................. 174/520, 174/539, 564, 650, 50
See application file for complete search history.

(56) References Cited

U.S. PATENT DOCUMENTS

| | | | |
|---|---|---|---|
| 4,654,470 A * | 3/1987 | Feldman et al. ............... | 174/50 |
| 5,256,834 A * | 10/1993 | Gehring ...................... | 174/37 |
| 6,128,193 A * | 10/2000 | Moss et al. .................. | 361/729 |
| 6,344,612 B1 * | 2/2002 | Kuwahara et al. .............. | 174/50 |
| 6,362,421 B1 * | 3/2002 | Layton, Jr. ................... | 174/50 |
| 6,586,674 B2 * | 7/2003 | Krause et al. ............... | 174/50.5 |
| 7,442,873 B2 * | 10/2008 | McCormick et al. .......... | 174/50 |
| 2005/0269140 A1 * | 12/2005 | Cox et al. .................... | 177/238 |

FOREIGN PATENT DOCUMENTS

| JP | 11-074032 A | 3/1999 |
|---|---|---|
| JP | 2002-039666 A | 2/2002 |

* cited by examiner

*Primary Examiner*—Hung V Ngo
(74) *Attorney, Agent, or Firm*—Marvin A Motsenbocker; Mots Law, PLLC

(57) ABSTRACT

Provided is a cover used for a thermostatic apparatus including an inner chamber enclosed with a plurality of walls and a temperature/humidity controller for controlling temperature and humidity in the inner chamber. The cover forms a space with a wall of the plurality of walls by being attached to the wall so as to cover a hole provided in the wall. The cover includes a opening through which a cord-shaped body passes, the cord-shaped body extending from the outside of the inner chamber to the inside thereof through the hole, a peripheral part being in hermetic contact with the wall; a contact part being in hermetic contact with the cord-shaped body in the opening; and a sealant being in hermetic contact with the hole. The cord-shaped body is led through the sealant in hermetic state, and a part of the cord-shaped body is housed in the space.

2 Claims, 8 Drawing Sheets

FRONT DOOR OF INCUBATOR

THERMOSTATIC APPARATUS AND COVER

BACKGROUND OF THE INVENTION

1. Field of the Invention

The present invention relates to a cover attached on a wall for leading a cable or the like to the inside of a thermostatic apparatus, such as an operation apparatus or a storage apparatus, and also relates to a thermostatic apparatus using the cover.

2. Description of the Related Art

Recently, in the biotechnology field or the like, thermostatic apparatuses, such as a storage apparatus called an incubator, and the like have been used in which environmental conditions thereof such as temperature and humidity can be kept constant for culturing cells. In the incubator, samples or the like are stored in an inner chamber (hereinafter referred to as a storage chamber) enclosed with multiple walls and having, for example, a rectangular-parallelepiped shape. The environmental conditions in the storage chamber can be kept constant. In the meantime, isolators have been used as thermostatic apparatuses. An isolator is an operation apparatus which allows experiments or operations to be performed in an inner chamber (hereinafter referred to as an operation chamber) by use of operation means. The operation chamber is enclosed with multiple walls and has a rectangular-parallelepiped shape, and so on. The operation means includes: a robot hand installed inside the operation chamber; a glove which allows operations to be performed in the operation chamber through an operation hole communicating with the operation chamber; and the like. Accordingly, such use of an isolator as a thermostatic apparatus enables experiments and operations to be performed under constant conditions in which temperature, humidity, and the like are kept constant.

The outer enclosures of these apparatuses, the storage chambers or operation chambers inside the outer enclosures, and the like have so called sealing capability against the surroundings. This sealing capability minimizes chemical and biological influences from the surroundings. In addition, these components have heat insulated structures. With the sealing capability and the heat insulated structure, these apparatuses including a temperature/humidity controller for controlling the temperature and humidity therein can thus keep their internal environments in desired constant conditions. Note that, in the isolators, operation means, such as the above-described glove has sealing capability.

The environment in the above-described inner chambers (hereinafter referred to as internal environment) is highly humid. For example, the temperature in the inner chambers is generally approximately 37° C., and the humidity is 80% or more. In some case, the humidity reaches 95%.

In order to lead a cable into the inner chamber, that is, the operation chamber or the storage chamber, from the outside, the outer enclosure needs to have at least one hole, thorough which the cable is led into the inner chamber from the outside. Examples of the cable (hereinafter generally referred to as a cord-shaped body) include a lead wire, an optical fiber cable, a tube, and the like connected to a measuring instrument or a controlling instrument. The measuring instrument and the controlling instrument are used for performing operations in the operation chamber, culturing cells in the storage chamber, or the like.

Since the cord-shaped body is led into the operation chamber or the storage chamber from the outside, the temperature of the cord-shaped body is generally lower than that of the internal environment. This may lower the temperature of the internal environment. In addition, since the temperature of the cord-shaped body is lower than that of the internal environment and the internal environment is highly humid, condensation may occur on the cord-shaped body in the operation chamber or the storage chamber. Moisture attributable to the condensation may allow growth of various bacteria and molds in the operation chamber or the storage chamber. However, the incubator and the isolator need to keep sealing capability against chemical and biological influences. Accordingly, to avoid such growth of various bacteria and molds or the like in the incubator and the isolator, the condensation on the cord-shaped body needs to be avoided. In addition, the moisture may cause deterioration of the cord-shaped body or corrosion of the apparatus. Thus, also in this respect, condensation on the cord-shaped body needs to be avoided.

Japanese Patent Application Publication No. 2002-39666 discloses a refrigerator in which condensation on a lead wire is suppressed by causing the lead wire to be in contact with a heat pipe installed in an external box of the refrigerator.

Japanese Patent Application Publication No. H11-074032 discloses a thermostatic bath in which temperature drop of a component is prevented by the following mechanism. Specifically, a cable housing room is provided under a socket mounting plate, and air is circulated in the cable housing room through an inlet and an outlet. Accordingly, a cable connected to a socket of the component located at the socket mounting plate is heated, and the temperature drop of the component by heat dissipation from the cable become suppressed.

According to the conventional technique disclosed in Japanese Patent Application Publication No. 2002-39666, however, in order to prevent condensation on the lead wire, the refrigerator needs to have a built-in mechanism such as the heat pipe to be in contact with the lead wire. Accordingly, there is a problem that, in a refrigerator without the built-in mechanism, condensation on the lead wire can not be prevented in such a way, once the production of the refrigerator is completed.

According to the conventional technique disclosed in Japanese Patent Application Publication No. H11-074032, air is circulated between the cable housing room and the thermostatic bath through the inlet and the outlet. As a result, water vapor around the cable does not decrease. Accordingly, there is a problem that condensed moisture keeps increasing in a case where the condensation is caused in the cable housing room due to the temperature drop of a cable surface caused by heat dissipation outside the cable room.

SUMMARY OF THE INVENTION

In view of the above-described problems, an object of the present invention is to prevent condensation on a cord-shaped body led into an operation apparatus or a storage apparatus. Another object of the present invention is to provide a thermostatic apparatus and a cover both of which enable prevention of condensation on a cord-shaped body led into an operation apparatus or a storage apparatus, even when these apparatuses do not have the built-in mechanism for preventing condensation on the cord-shaped body.

A thermostatic apparatus according to the present invention includes: an inner chamber enclosed with a plurality of walls; a temperature/humidity controller for controlling temperature and humidity in the inner chamber; and a cover attached to a wall of the plurality of walls so as to cover a hole provided in the wall, the cover having a space between the cover and the wall, the cover including: a opening through which a cord-shaped body passes, the cord-shaped body extending from the outside of the inner chamber to the inside thereof through the hole, a peripheral part being in hermetic contact with the wall: a contact part being in hermetic contact with the cord-shaped body in the opening; and a sealant being in hermetic contact with the hole, the cord-shaped body is led through the sealant in hermetic state, and a part of the cord-shaped body is housed in the space.

A cover according to the present invention is used for a thermostatic apparatus including an inner chamber enclosed with a plurality of walls and a temperature/humidity controller for controlling temperature and humidity in the inner chamber, and forming a space with a wall of the plurality of walls by being attached to the wall so as to cover a hole provided in the wall, the cover comprising: a opening through which a cord-shaped body passes, the cord-shaped body extending from the outside of the inner chamber to the inside thereof through the hole, a peripheral part being in hermetic contact with the wall; a contact part being in hermetic contact with the cord-shaped body in the opening; and a sealant being in hermetic contact with the hole, the cord-shaped body is led through the sealant in hermetic state, and a part of the cord-shaped body is housed in the space.

The cord-shaped body represents a long thin body like a cord and examples thereof include a cable (such as a lead wire or an optical fiber cable), a duct, a tube or the like which is typically used in a measuring instrument or the like. A part of the cord-shaped body is stored in a housing space, while banded in a meandering manner or a coiled manner. The cord-shaped body may be led in and out through a single hole; alternatively, the cord-shaped body may be led in through one hole and led out through another hole.

The terms "sealing capability", "hermetic", and "hermetically" are used to describe a hermetic state that is regarded as being chemically and biologically sealed from the surroundings or a state in which chemical and biological influences from the surroundings are minimized.

The present invention makes it possible to prevent condensation on a cord-shaped body led into an operation apparatus, a storage apparatus, or the like. In addition, installation of the cover of the present invention enables the prevention of condensation on a cord-shaped body led into an operation apparatus or a storage apparatus, even when these apparatuses do not have the built-in mechanism for preventing condensation on the cord-shaped body.

Meanings and effects of the present invention will be further apparent from the following description on an embodiment of the present invention.

Note that the following embodiment is a mere embodiment of the present invention. Therefore, the present invention and meanings of terms for constituent features of the present invention are by no means limited to those described in the following embodiment.

DESCRIPTION OF THE PREFERRED EMBODIMENT

Hereinafter an embodiment of the present invention will be described with reference to the drawings.

Figure 1A:
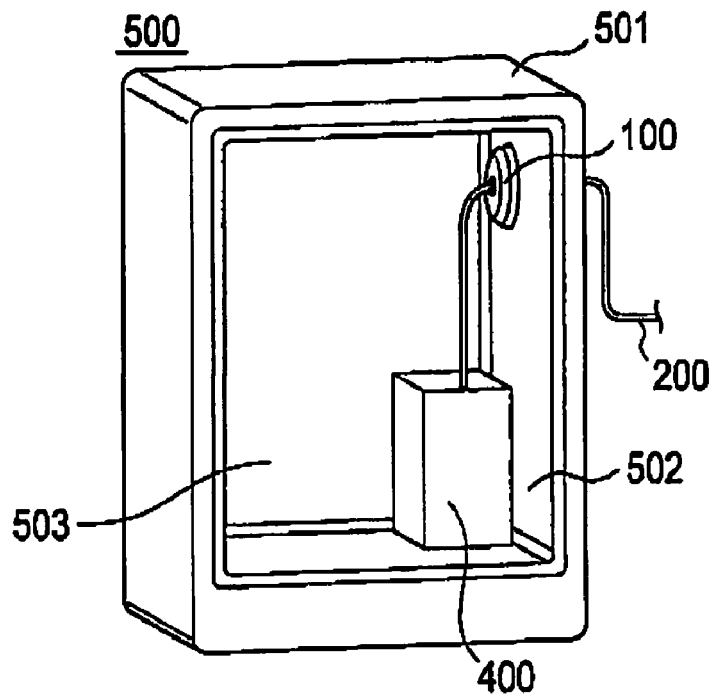
FIGS. 1A and 1B show an incubator according to an embodiment.
Figure 1B:
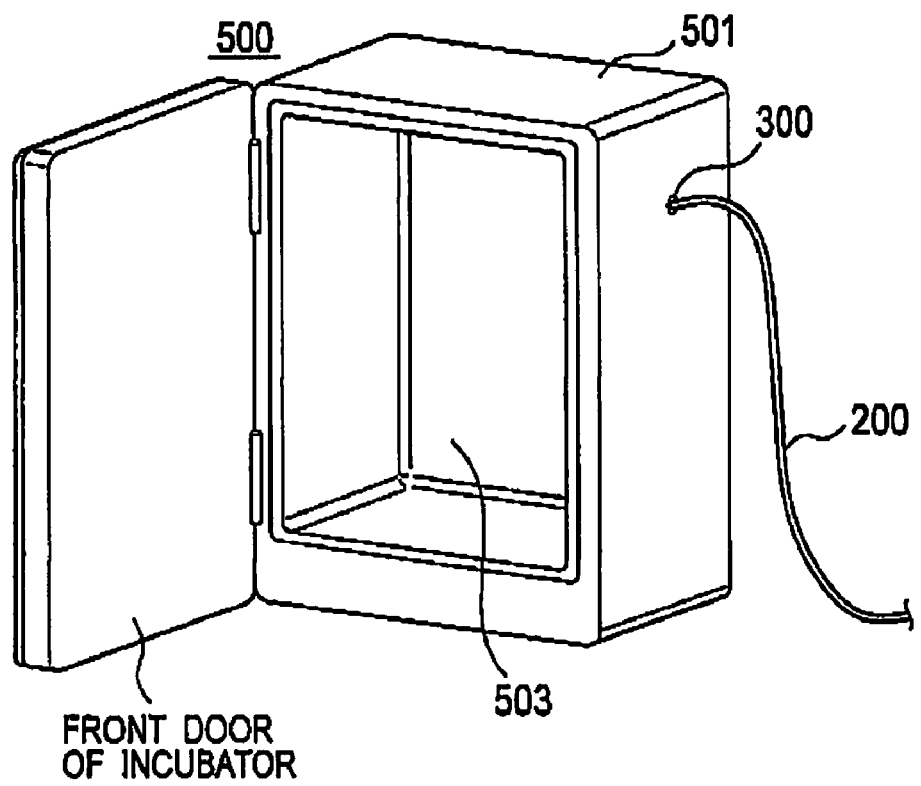

FIGS. 1A and 1B show an anti-condensation cover 100 according to the embodiment hermetically attached to an incubator 500. FIG. 1A is a left-front view of the incubator. FIG. 1B is a right-front view of the incubator. In FIG. 1A, the front door of the incubator is not shown for the sake of description.

As shown in FIGS. 1A and 1B, the incubator 500 includes a storage chamber 503 inside an outer enclosure 501. The anti-condensation cover 100 according to the embodiment is attached to a wall 502 so as to cover a hole 300. The hole 300 is provided in the wall 502 that is one of the walls enclosing the storage chamber 503. A cable 200, which is a cord-shaped body, is led from the outside of the outer enclosure 501 through the hole 300 into the hermetically-sealed storage chamber 503 in the incubator 500. Since the storage chamber 503 needs to be kept at a constant temperature, a temperature/humidity controller performing control for keeping, for example, the inside temperature and humidity constant is provided in the outer enclosure 501. The cable 200 is led from the inside to the outside of the anti-condensation cover 100. Note that the wall 502 has built-in heaters that are not shown in FIGS. 1A and 1B. The heater heats the storage chamber 503 under the control of the temperature/humidity controller.

The anti-condensation cover 100 of this embodiment has a shape of a dome, and a space (hereinafter refereed to as a cable housing) between the anti-condensation cover 100 and the wall 502. The anti-condensation cover 100 has an opening penetrating the top of the dome. The cable 200 extends from the opening at the top. Note that the shape of the cover is not limited the dome shape, and any shape can be employed according to a place to which the cover is attached. The peripheral part of the dome shape of the anti-condensation cover 100 is brought into contact with the wall 502, and hermetically attached to the wall 502. Note that the sealing capability between the cover and the wall 502 is provided in the following manner. Specifically, the cover is fixed with screws and screw holes for fixation provided around the hole 300, is bonded by an adhesive, or is attached by use of magnets or suction cups. Examples of the cable 200 include a measurement probe, a lead wire, a power supply cable, an optical fiber cable, a duct, a tube, and the like which are connected to a stationary instrument 400, such as a measuring instrument, a reagent supplying apparatus, a heater, or the like, used for measurements or experiments. The cable 200 is in hermetic contact with the cover 100.

Figure 2A:
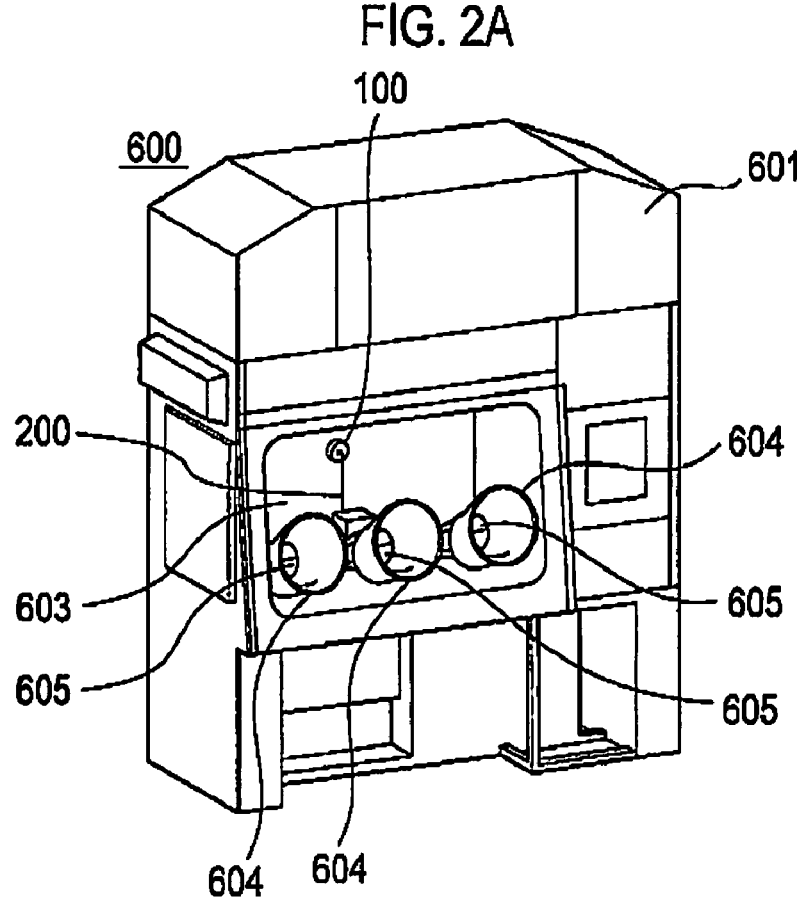
FIGS. 2A and 2b show an isolator according to an embodiment.
Figure 2B:
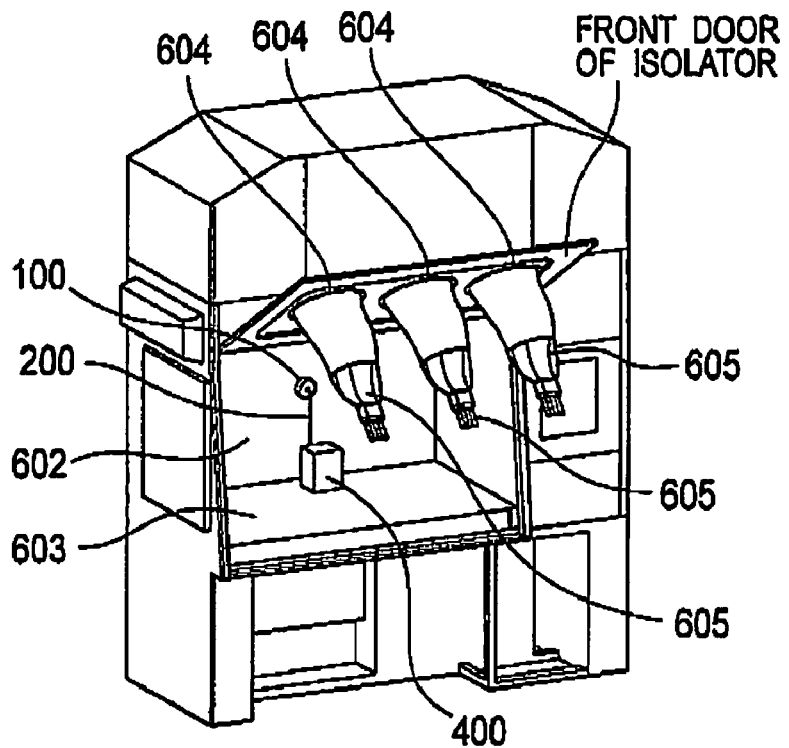

FIGS. 2A and 2B show an anti-condensation cover 100 according to the embodiment hermetically attached to an isolator 600. In some cases, the isolator 600 is used for performing operations under thermostatic conditions where the environments of experiments such as temperature, humidity, and the like are kept constant. Here, description will be made of such an application as an example.

FIG. 2A shows the isolator 600 in a state where a front door thereof is closed and operations can be performed. FIG. 2B shows the isolator 600 in a state where the front door thereof is open and the inside of the isolator 600 can be viewed.

As shown in FIGS. 2A and 2B, the isolator 600 includes an operation chamber 603 inside an outer enclosure 601. The anti-condensation cover 100 according to the embodiment is attached to a wall 602 so as to cover a hole (not shown). The hole is provided in the wall 602 that is one of the walls enclosing the operation chamber 603. A cable 200 is led from the outside of the outer enclosure 601 through the hole into the hermetically-sealed operation chamber 603 in the isolator 600. Since the operation chamber 603 needs to be kept at a constant temperature, a temperature/humidity controller performing control for keeping, for example, the inside temperature and humidity constant is provided in the outer enclosure 601. The cable 200 is led from the inside to the outside of the anti-condensation cover 100. Note that the wall 602 has a built-in heater that is not shown in FIGS. 2A and 2B. The heater heats the operation chamber 603 under the control of the temperature/humidity controller.

The anti-condensation cover 100 and the cable 200 are the same as those in the description of the incubator 500. Experiments or operations can be performed in the operation chamber 603 of the isolator 600. For the experiments or operations, operation means 605, such as gloves, is used which allows operations in the operation chamber 603 to be performed through operation holes 604 communicating therewith. Note that the operation means 605 and the operation holes 604 can have sealing capability.

In the incubator 500 shown in FIGS. 1A and 1B and the isolator 600 shown in FIGS. 2A and 2B, condensation on a cord-shaped body, such as a cable, led into the incubator or the isolator can be prevented because of reasons to be described later. In addition, installation of the above-described anti-condensation cover to the operation apparatus, the storage apparatus, or the like enables prevention of condensation on a cable led into these apparatuses, even when these apparatuses do not have a built-in mechanism for preventing condensation.

In addition, the cover can have sealing capability. Accordingly, because of reasons to be described later, humid air does not flow into the cover, and thus the condensation inside the cover can be limited to a certain level. Furthermore, the condensed moisture in the cover is prevented from flowing into the inner chamber.

Note that, because of reasons to be described later, these apparatuses have an advantage that a separate heat source for providing the cover with heat for preventing condensation is not required since the cover covers the wall in the region where the above-described built-in heater is provided.

Next, description will be made of the anti-condensation cover.

Figure 3:
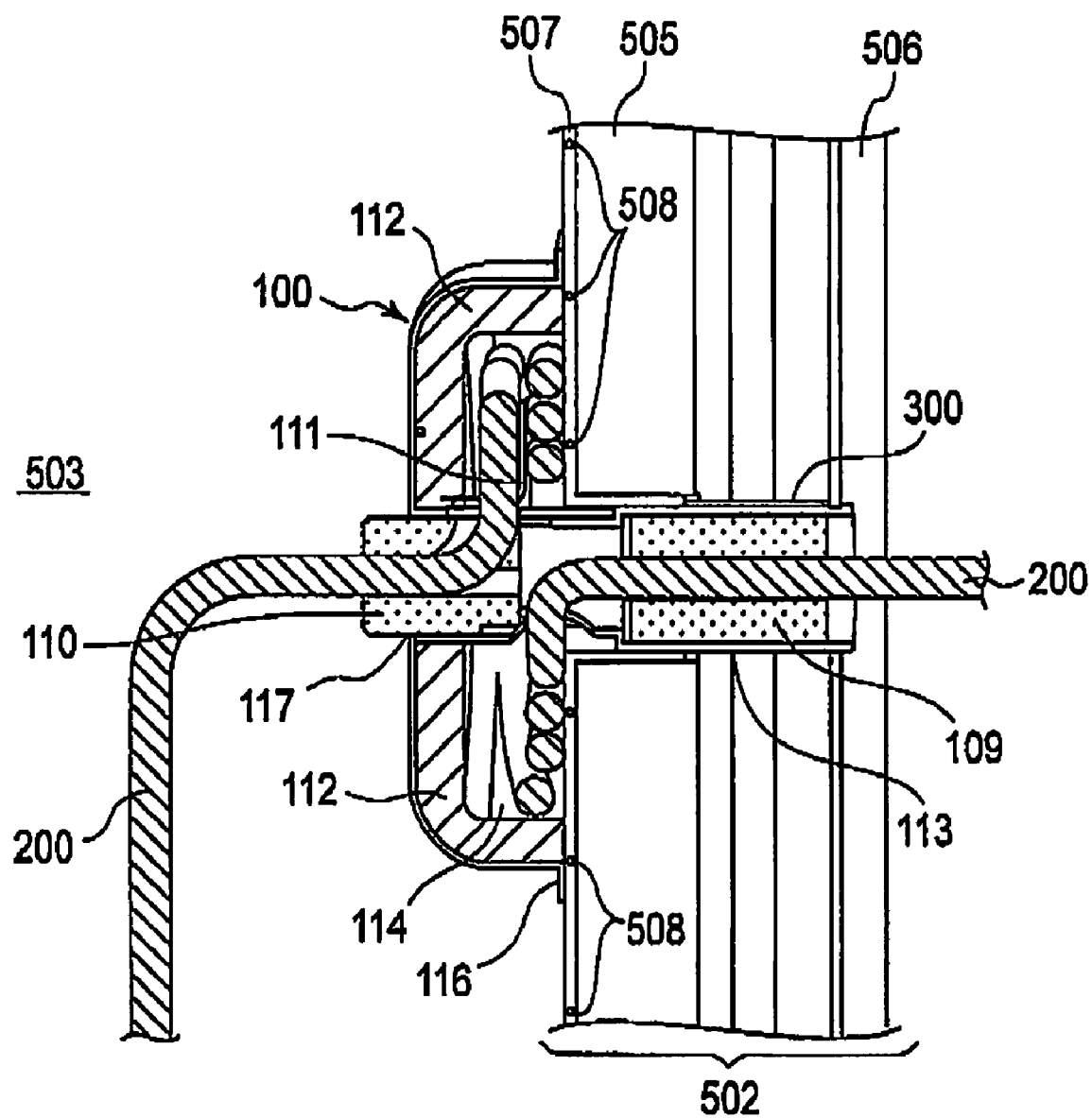
FIG. 3 is a cross-sectional view of an anti-condensation cover according to an embodiment.

FIG. 3 is a cross-sectional view of the anti-condensation cover 100 according to the embodiment. The anti-condensation cover 100 includes an opening 117 and a peripheral part 116. The opening 117 is located at the top of the above-described dome shape of the anti-condensation cover 100. The opening 117 of this embodiment is circular. The peripheral part 116 of this embodiment is ring-shaped, and is located in the periphery of the dome shape. The shape of the opening is not limited to a circle, and the shape of the peripheral part is not limited to a ring. Any shapes can be employed for the opening and the peripheral part in accordance with the cross-sectional shape of the cable, the shape of the inner chamber, and the shape of the wall, and the like. The peripheral part 116 is in hermetic contact with the wall 502.

FIG. 3 is a vertical cross-sectional view of the anti-condensation cover 100 having a dome-like outer shape. The cross-sectional view is taken along the line connecting the center of the circular shape of the opening 117 and the center of the ring shape of the peripheral part 116 of the cover 100 attached to the incubator 500.

The anti-condensation cover 100 includes a heat insulator 112. The cable 200 is led through the opening 117 with a packing 110 interposed therebetween for securing sealing capability. Accordingly, the packing 110 represents a contact part of the present invention being in hermetic contact with the cable 200.

Note that, in this embodiment, the anti-condensation cover 100 includes a single opening (the opening 117); however, the anti-condensation cover 100 may include multiple openings (not shown). The multiple openings of the anti-condensation cover 100 allow multiple cables 200 to be led from the outside to the inside of the inner chamber through a hole in the wall and then through respective openings.

The hole 300 is provided in the wall 502, and a cable cap 113 including a heat insulator 109 therein is hermetically fitted into the hole 300. Note that the cable cap 113 represents the sealant of the present invention being in hermetic contact with the hole. The cable 200 covered with the heat insulator 109 is led through the hole 300 from the outside of the incubator 500 to the storage chamber 503 therein.

Note that in this embodiment, the wall 502 includes a single hole (the hole 300); however, the wall 502 may include multiple holes (not shown). The multiple holes in the wall 502 allow multiple cables to be led from the outside to the inside of the incubator. It is possible to lead multiple cables through one hole. However, in such case, the diameter of the hole becomes greater in accordance with the number of cables used. This affects the sealing capability of the hole. In addition, multiple holes may be provided in different walls. This allows multiple cables to be led from the outside to the inside of the incubator as similar to the above-described case.

The cable housing 114 is a space enclosed by the dome-shaped cover 100 and the wall 502. A part of the cable 200 is stored in the cable housing 114, while banded in a meandering manner or a coiled manner. The load of the part of the banded cable 200 is supported by a cable stopper 111, or the part of the banded cable 200 is pressed by the cable stopper 111 toward the wall 502. Since the part of the cable 200 is pressed by the cable stopper 111 toward the wall 502, heat is conducted to the part of the cable 200 from an inner wall 507 heated by heaters 508 therein.

Note that FIG. 3 shows a cross-sectional view of the wall 502 of the incubator 500. The wall 502 includes layers of the inner wall 507, a heat insulator 505 and an outer crust 506. The inner wall 507 includes the built-in heaters 508. The heaters 508 and the heat insulator 505 make it possible to keep the inside temperature of the storage chamber 503 constant. Heat conduction from the heater 508 eliminates the need for a separate heat source in the cover 100 for heating the inside of the cable housing 114 and the part of the cable 200 stored in the cable housing 114. In other words, the cover 100 needs no separate heat source to prevent condensation.

Figure 4A:
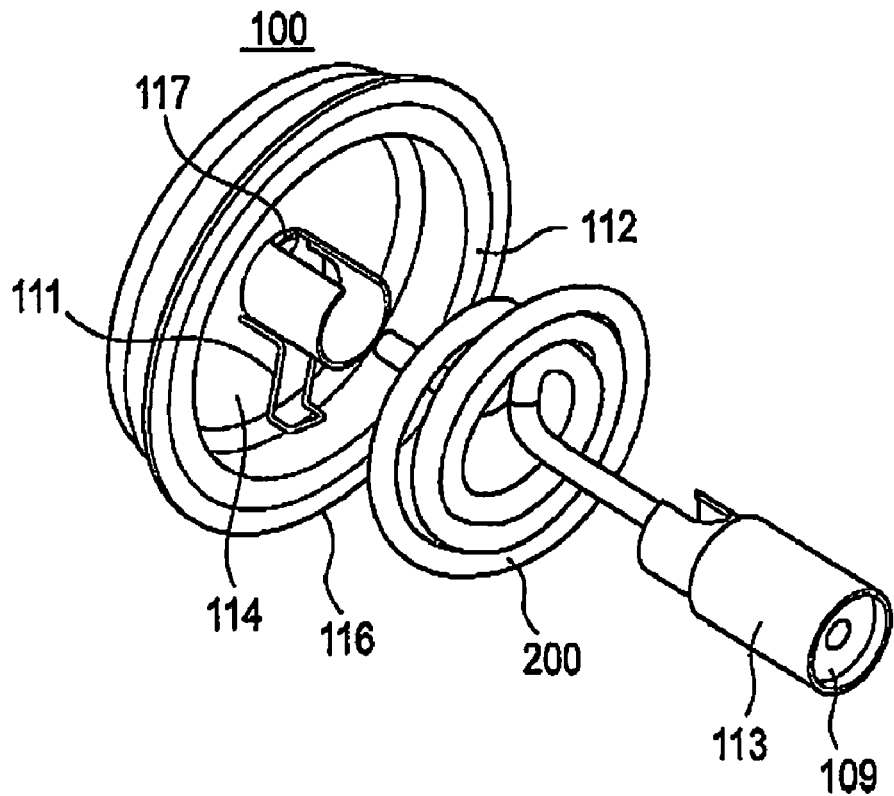
FIGS. 4A and 4B are perspective views of the anti-condensation cover according to an embodiment.
Figure 4B:
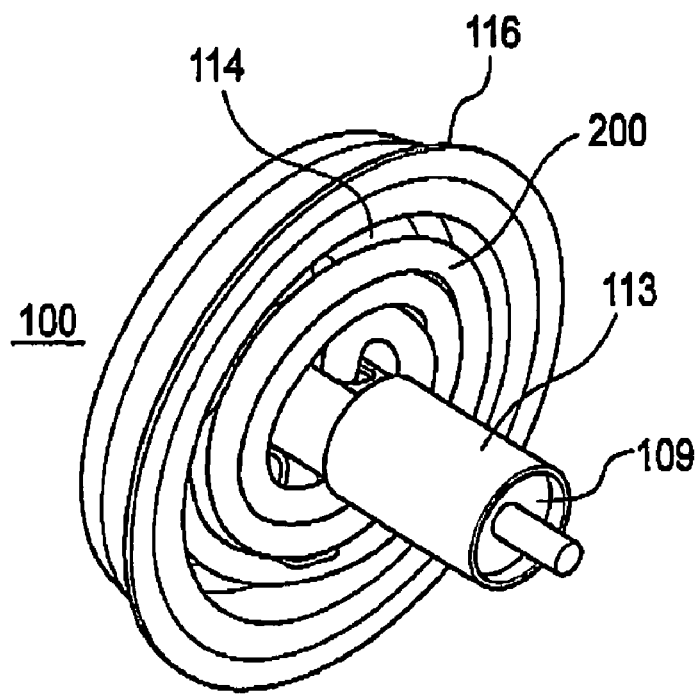

FIGS. 4A and 4B show the part of the cable 200 banded in a coiled manner in a state before (FIG. 4A) and after (FIG. 4B) housing of the cable 200 in the cable housing 114, viewed from the peripheral part 116 side. Reference numerals in FIGS. 4A and 4B denote, respectively, the same constituents as those in FIG. 3 and the like. The cable 200 is banded in a coiled manner with such a curvature that no stress is caused in the cable. The part of the cable 200 may be banded in a meandering manner with such a curvature that no stress is caused in the cable.

Figure 5A:
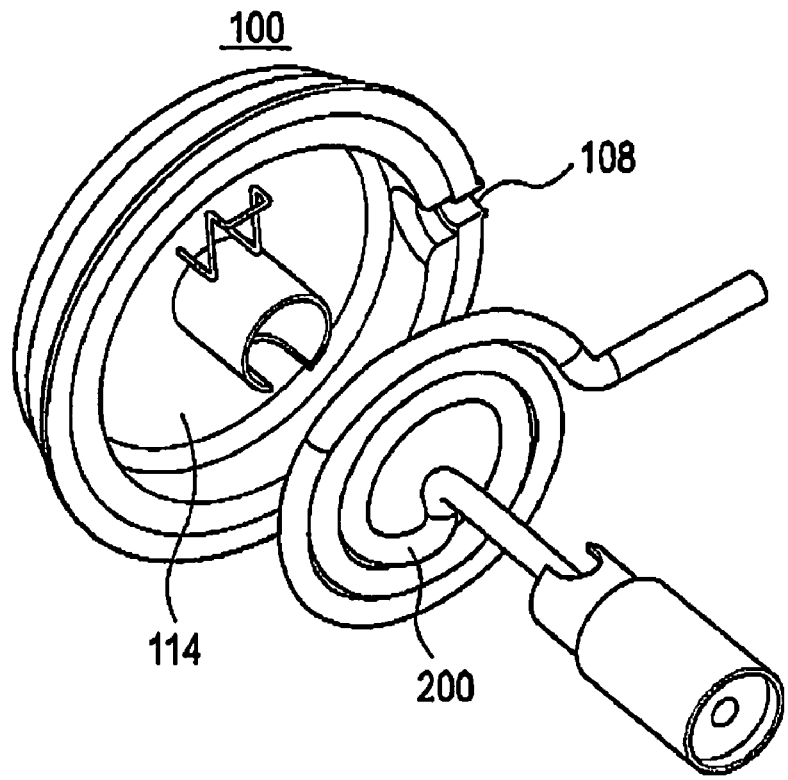
FIGS. 5A and 5B are perspective views of an anti-condensation cover according to an embodiment.
Figure 5B:
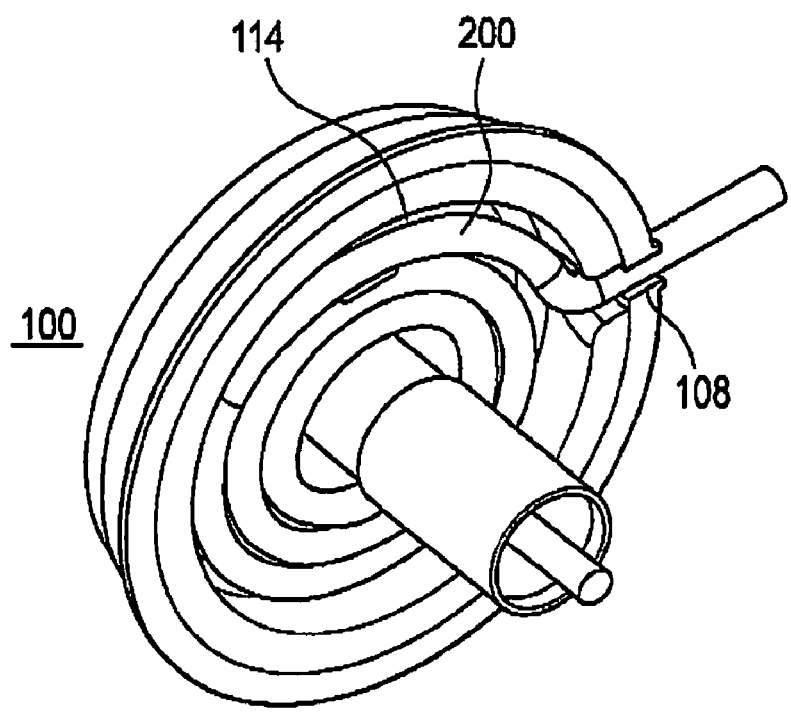

Note that, FIGS. 5A and 5B show an example of a case where the opening and the peripheral part 116 of anti-condensation cover 100 are continuous with each other. FIG. 5A shows the part of the cable 200 banded in a coiled manner in a state before housing of the cable in the cable housing 114r while FIG. 5B shows the part of the cable 200 banded in a coiled manner in a state after housing of the cable in the cable housing 114. Reference numerals in FIGS. 5A and 5B denote, respectively, the same constituents as those in FIG. 3 and the like. The cable is banded in a coiled manner with such a curvature that no stress is caused in the anti-condensation cover 100; alternatively, the cable may be banded in a meandering manner. The opening 117, for example, has such a shape that a notch 108 located in the side surface of the anti-condensation cover 100 is formed in the above-described peripheral part 116 as shown in FIGS. 5A and 5B. Note that the notch 108 corresponds to the opening. In other words, the anti-condensation cover 100 in FIGS. 5A and 5B includes no opening at the top of the dome. The cable 200 extends from the notch 108 to the outside of the anti-condensation cover 100.

In FIGS. 3, 4A and 4B, it is described that the part of the cable 200 is stored in the housing 114. When the length L of the stored part of the cable 200 is shorter than a certain length Lth, the surface temperature of the stored part of the cable 200 may not be sufficiently increased inside the anti-condensation cover 100. Accordingly, condensation may occur on a portion of the cable 200 just outside the anti-condensation cover 100. To prevent this, the length L of the part of the cable 200 stored in the anti-condensation cover 100 needs to be longer than a certain length Lth. Hereinafter, description will be given of a method for calculating the certain length Lth for the incubator, for example; however, the method for calculating the certain length Lth is not limited thereto.

Figure 6A:
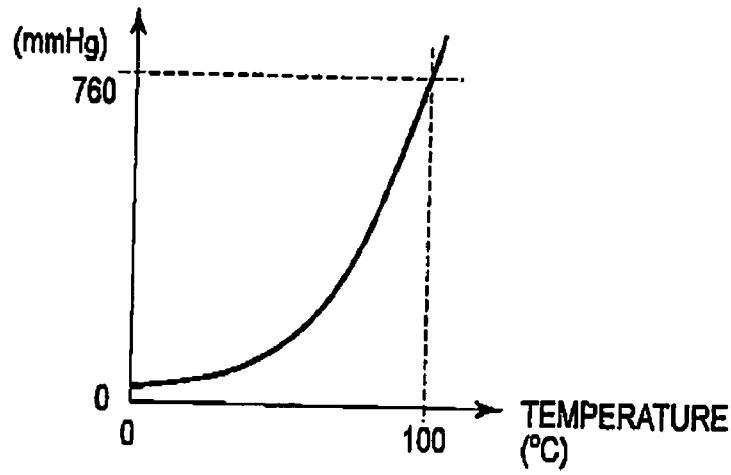
FIGS. 6A and 6B shows relationship between temperature and saturation vapor pressure as well as temperature characteristics near the surface of a cable according to an embodiment.
Figure 6B:
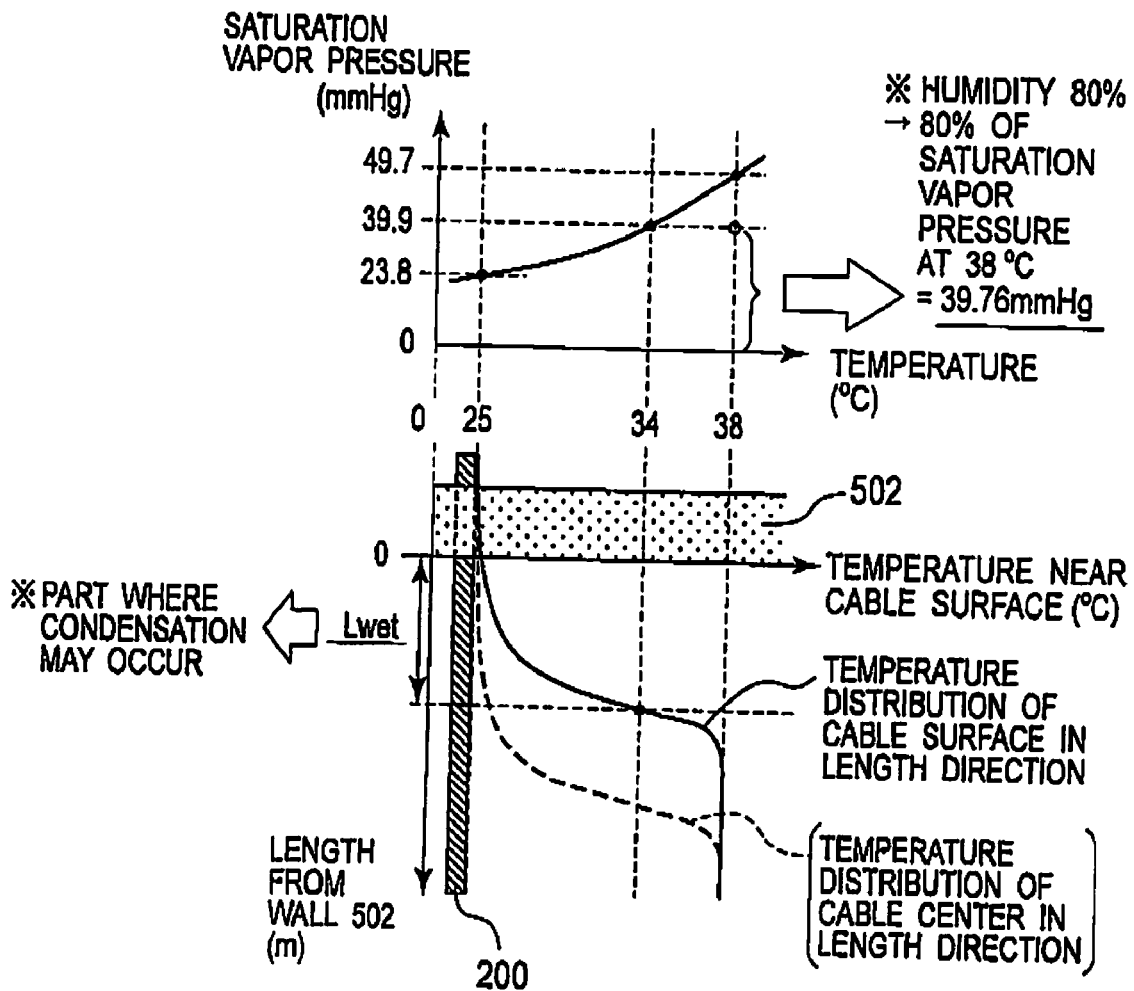

FIG. 6A is a characteristic diagram (graph) showing the outline of the relationship between temperature and saturation vapor pressure. FIG. 6B is an enlarged diagram of a portion of the characteristic diagram and the like. Note that, in the following description, a case where the inside environment of the incubator is at a temperature of 38° C. and a humidity of 80% is taken as an example.

FIG. 6A is the characteristic diagram of the saturation vapor pressure at a temperature ranging from 0° C. to 100° C. under a pressure of 1 atm. In FIG. 6A, the horizontal axis represents temperature, and the vertical axis represents saturation vapor pressure.

The upper part in FIG. 6B is an enlarged diagram of the characteristic diagram shown in FIG. 6A. The upper part shows characteristics of saturation vapor pressure at a temperature ranging from 25 to 38° C. and the region where condensation may occur. In the upper part in FIG. 6B, the horizontal axis represents temperature, and the vertical axis represents saturation vapor pressure.

On the other hand, the lower part in FIG. 6B shows the temperature distribution in the length direction of the cable extending from the wall 502 to the inside of the incubator. The temperature near the cable surface is assumed to be the same as that on the cable surface. In the lower part in FIG. 6B, the horizontal axis represents the temperature near the cable surface, and the vertical axis represents the length L of the cable from the wall 502 (the length L of the cable inside the incubator increases in the downward direction of the vertical axis). For this case, which part of the cable surface are subjected to condensation will be discussed.

Suppose that, at the length denoted by L=Lwet, the surface temperature of the cable is 34° C. As shown in FIG. 6B, at a length in a range 0<L<Lwet, the surface temperature of the cable is below 34° C. This suggests that the air temperature near the cable surface at a length in a range 0<L<Lwet is below 34° C. This means that, according to the calculation, the amount of water vapor in the air near the cable surface at a length in a range 0<L<Lwet exceeds the amount corresponding to the saturation vapor pressure. However, in actuality, the amount of water vapor in the air cannot exceed the amount corresponding to the saturation vapor pressure. Water vapor exceeding the amount corresponding to the saturation vapor pressure is liquefied. This means that condensation occurs on the cable surface at a length in a range 0<L<Lwet.

Accordingly, the certain length Lth should be equal to or greater than Lwet, according to the calculation. However, this calculation is made for an ideal case where the temperature of the air around the cable shows a temperature gradient in the length direction of the cable in accordance with the temperature distribution of the cable surface. In actuality, since the air circulates, the ideal temperature gradient as described above cannot be achieved normally. Therefore, in practical, the Lth should be somewhat greater than Lwet.

As described above, the length Lth (Lwet) can be calculated by a simulation of temperature distribution near the cable surface using the temperature and the humidity inside the incubator, the temperature outside the incubator, and the temperature distribution on the cable surface. One example of simulation results will be described below.

Figure 7A:
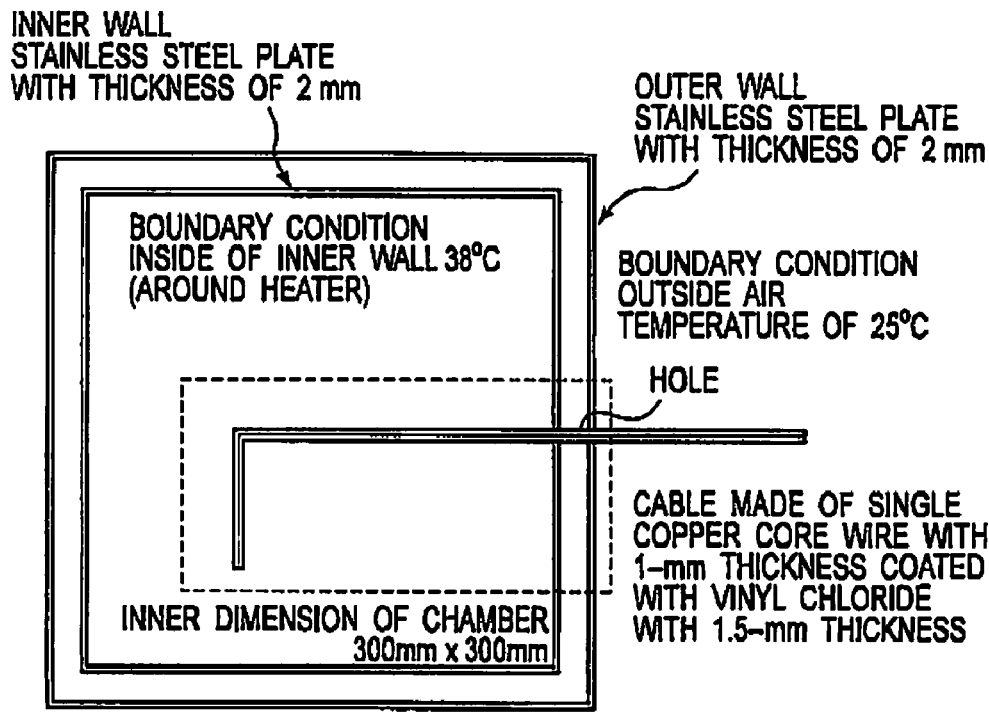
FIGS. 7A and 7B are diagrams showing simulation results of temperature distribution of the surface and the inside of a cable according to an embodiment.
Figure 7B:
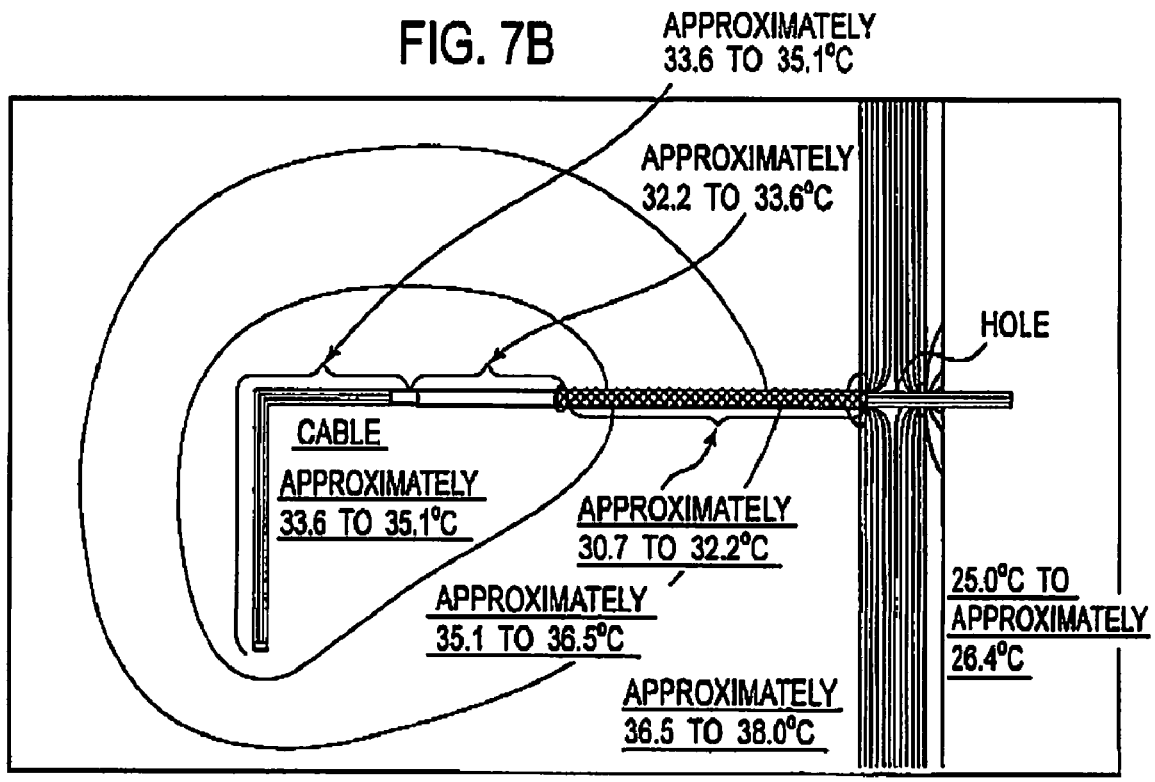

FIGS. 7A and 7B show the simulation result of the temperature distribution of the surface and the inside of the cable in the incubator into which the cable is led from the outside to the inside. Note that FIGS. 7A and 7B also show simulation results of temperature distributions of the inner wall, the inside air, and outside air of the incubator.

In addition, the temperature outside the incubator in FIG. 7A is 25° C., and the heater temperature in the wall of the incubator in FIG. 7A is 38° C. FIG. 7A shows simulation conditions such as the boundary conditions of the simulation, and dimensions of the storage chamber. FIG. 7B shows the simulation results of the temperature distributions of the cable, the inside of the storage chamber and the outside of the incubator. Note that FIG. 7B is an enlarged diagram showing the simulation results of the temperature distributions in the area enclosed by the dotted line.

The simulation preconditions are as follows.

The cable has a double-layered structure. The core wire of the cable is made of a single copper wire, and has a diameter of 1 mm and a heat conductivity of 420 W/mK. The coating of the cable is made of vinyl chloride, and has a thickness of 1.5 mm and a heat conductivity of 0.14 W/mK. Heaters are provided in the inner walls of the incubator, and the temperature of the inner walls provided with the heater is 38° C. Each of the inner walls of the incubator includes therein a dual structure formed of air (with a heat conductivity of 0.02 W/mK) serving as a heat insulator, and a stainless steel (with a heat conductivity of 41 W/mK). Calculation is made under these preconditions. As shown in FIG. 7A, the inner walls, i.e., walls of the storage chamber are made of stainless steel plates with a thickness of 2 mm, and the outer walls, i.e., the outer enclosure of the incubator are made of stainless steel plates with a thickness of 2 mm. The inner dimensions of the storage chamber are 300 mm in height and 300 mm in length from the hole.

The cable has an L-shape, as shown in FIGS. 7A and 7B. The entire length of the L-shaped portion is approximately 28 cm, and the cable is bent at a position approximately 20 cm away from the hole in the inner wall. The cable inside the incubator is not in contact with the inner wall of the incubator.

According to the simulation results shown in FIG. 7B, the temperature distributions of the surface and the inside of the cable are described as follows: a region in an approximate temperature range of 30.7 to 32.2° C.; a region in an approximate temperature range of 32.2 to 33.6° C.; a region in an approximate temperature range of 33.6 to 35.1° C., in this order from the region closest to the hole of the inner wall of the incubator. Note that the temperature on the cable surface tends to be higher than that of the inside of the cable. As described above, most parts of the cable surface except the part at the tip of the cable have a temperature below 34° C. In combination with the description made in FIGS. 6A and 6B, the simulation results show that condensation may occur in most parts of the surface of the cable inside the incubator.

Figure 8A:
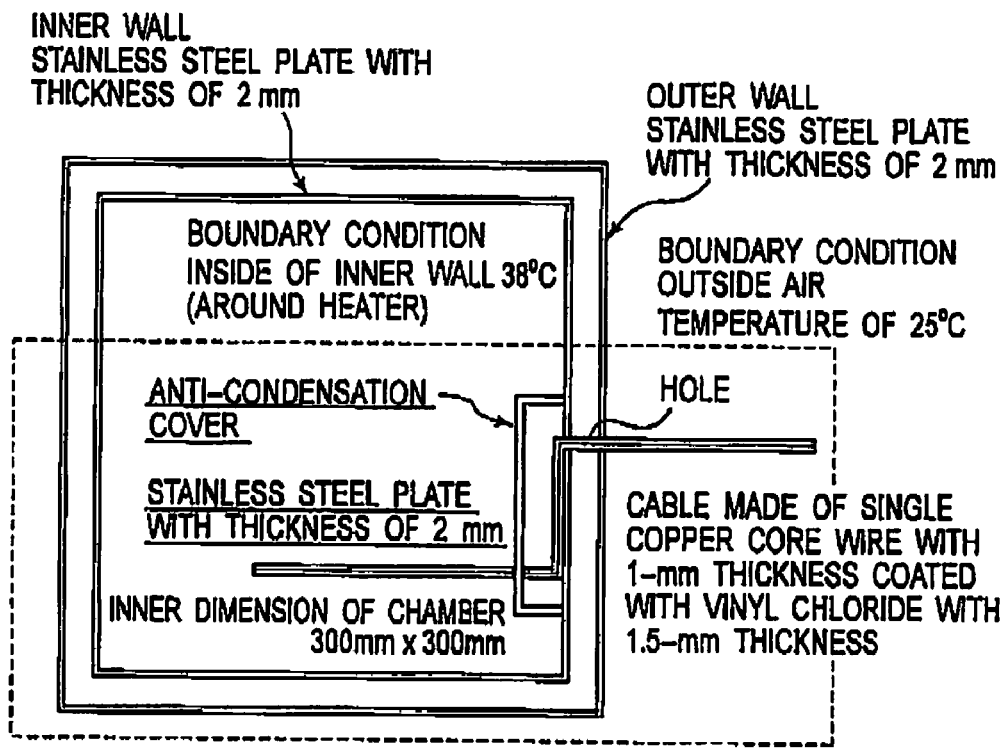
FIGS. 8A and 8B are diagrams showing simulation results of temperature distributions of the surface and the inside of a cable according to an embodiment.
Figure 8B:
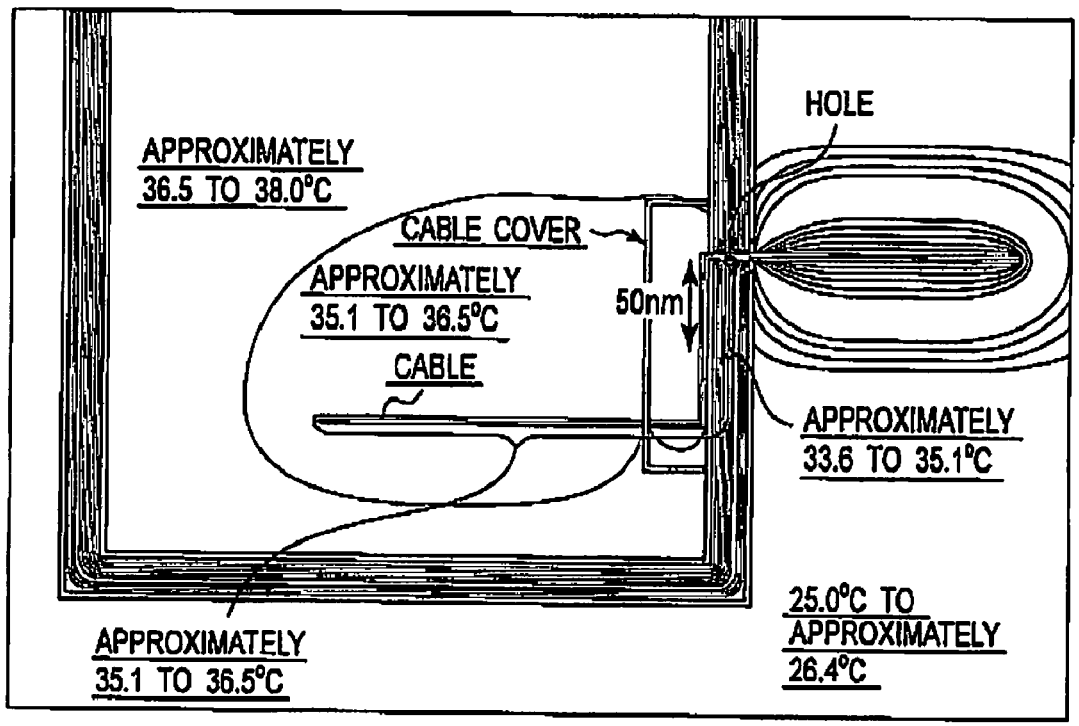

FIGS. 8A and 8B show simulation results of the temperature distributions of the surface and the inside of a cable which is also led from the outside to the inside of the incubator. Note that FIGS. 5A and 5B show simulation results of temperature distributions of the inner wall, the inside air, and the outside air of the incubator.

The incubator in FIGS. 8A and 8B is different from that in FIGS. 7A and 7B in that the cover according to this embodiment is attached to the inner wall of the incubator. In the cover, a portion of the cable is in contact with the inner wall of the incubator.

FIG. 8A shows simulation conditions such as the boundary conditions of the simulation, and dimensions of the storage chamber. FIG. 8B shows the simulation results of the temperature distributions of the cable, the inside of the storage chamber and the outside of the incubator. Note that FIG. 8B shows the simulation results of the temperature distributions in the area enclosed by the dotted line in FIG. 8A. The conditions described in FIG. 8A are the same as those described in FIG. 7A except that the anti-condensation cover is made of a stainless steel plate with a thickness of 2 mm.

In addition, the cable has a crank-shape as shown in FIGS. 8A and 8B. The entire length of the crank-shaped portion is approximately 28 cm, and the cable is bent at a position approximately 8 cm away from the hole in the inner wall. In the cover, a part of the cable (the part 8 cm away from or closer to the hole) is in contact with the inner wall of the incubator. The simulation preconditions are the same as those in FIG. 7, except the shape of the cable.

According to the simulation results shown in FIG. 8B, the temperature distributions of the surface and the inside of the cable are described as follows: a region in an approximate temperature range of 33.6 to 35.1° C.; and a region in an approximate temperature range of 35.1 to 36.5° C., in this order from the region closest to the hole of the inner wall of the incubator.

In a first portion of the cable within approximately 5 cm from the hole in the inner wall of the incubator, the temperatures of some points of the cable surface are below 34° C. The simulation results show that condensation may occur on the points of the cable with a surface temperature below 34° C. as described above with reference to FIG. 6B. Here, in a portion of the cable in contact with the wall of the incubator, a second portion (the portion excluding the first portion within approximately 5 cm from the hole in the inner wall of the incubator) of the cable have a surface temperature above 34° C., because the second portion is heated by the heaters in the inner wall of the incubator. Since the temperature of the core wire in the second portion of the cable is also 34° C. or above, the temperature of the surface of the second portion does not fall below 34° C. In addition, the first portion within approximately 5 cm from the hole in the inner wall of the incubator is housed in the cover according to this embodiment. Accordingly, condensation does not occur on the surface of the cable located outside the cover and inside the incubator. Here, suppose that condensation has occurred inside the cover. Even in such a case, the moisture never leaks into the inside of the incubator through the cover, since the anti-condensation cover 100 is hermetically attached to the wall with the periphery of the dome shape of the anti-condensation cover 100 being in contact with the wall.

Note that the first portion of the cable within approximately 5 cm from the hole in the inner wall of the incubator can be regarded as a portion within the above-described certain length Lwet. It is preferable that the length Lth be sufficiently longer than the 5-cm length, because of the above-described reasons.

The capacity of the housing 114 housing a part of the cable 200 may vary depending on the heat conductivities of the cable and the inner wall of the incubator, or the like; however, the capacity of the housing 114 is determined depending on at least the length of the cable determined in accordance with the temperature distribution of the cable surface, i.e., the above-described certain length Lth as well as the thickness (the radius or the diameter of the cable). In other words, the capacity of the housing 114 depends on at least the volume of the part of the cable stored in the housing 114.

Note that the capacity of the housing 114 in this case is close to the minimum possible value of the capacity of the housing 114. The capacity of the housing 114 should be determined so that the cable can be banded in a meandering manner with such a curvature that no stress is caused in the cable. In addition, the capacity of the housing 114 should be determined depending on the volume of the heat insulator in the anti-condensation cover 100, the size and shape of the cable stopper 111. In consideration of the above-described factors, the capacity of the housing 114 is desirably determined in the optimal capacity, while avoiding an excessively large value.

As described above, use of the anti-condensation cover 100 can prevent condensation on a cord-shaped body, such as a cable, led into a storage apparatus, such as an incubator, or an operation apparatus, such as an isolator. In addition, it is possible to provide the anti-condensation cover which is attached to a storage apparatus, such as an incubator, or an operation apparatus, such as an isolator, and which prevents condensation on a cord-shaped body, such as a cable, led into the storage apparatus or the operation apparatus, even when these apparatuses do not have a built-in mechanism for preventing condensation on the cord-shaped body.

In addition, since the cover includes the peripheral part being in hermetic contact with the wall, and the contact part being in hermetic contact with the cord-shaped body, humid air does not flow into the cover. Accordingly, the condensation inside the cover can be limited to a certain level. Furthermore, the condensed water in the cover is prevented from flowing into the inner chamber.

Note that the cover has an advantage that a separate heat source for preventing condensation is not required in the cover, since the cover covers the wall in the region where the built-in heaters are provided.

The embodiment of the present invention can be modified as appropriate within a range of technical ideas described in the scope of the claims in various ways.

What is claimed is:

1. A thermostatic apparatus comprising:
an inner chamber enclosed with a plurality of walls;
a temperature/humidity controller for controlling temperature and humidity in the inner chamber; and
a cover attached to a wall of the plurality of walls so as to cover a hole provided in the wall, the cover having a space between the cover and the wall, the cover including:
   a opening through which a cord-shaped body passes, the cord-shaped body extending from the outside of the inner chamber to the inside thereof through the hole,
   a peripheral part being in hermetic contact with the wall;
   a contact part being in hermetic contact with the cord-shaped body in the opening; and
   a sealant being in hermetic contact with the hole,
the cord-shaped body is led through the sealant in hermetic state, and
a part of the cord-shaped body is housed in the space.

2. A cover used for a thermostatic apparatus including an inner chamber enclosed with a plurality of walls and a temperature/humidity controller for controlling temperature and humidity in the inner chamber, and forming a space with a wall of the plurality of walls by being attached to the wall so as to cover a hole provided in the wall, the cover comprising:
   a opening through which a cord-shaped body passes, the cord-shaped body extending from the outside of the inner chamber to the inside thereof through the hole,
   a peripheral part being in hermetic contact with the wall;
   a contact part being in hermetic contact with the cord-shaped body in the opening; and
   a sealant being in hermetic contact with the hole,
   the cord-shaped body is led through the sealant in hermetic state, and
   a part of the cord-shaped body is housed in the space.

* * * * *